United States Patent [19]

Jamshidi

[11] 4,356,828

[45] Nov. 2, 1982

[54] BONE MARROW ASPIRATION NEEDLE

[76] Inventor: Khosrow Jamshidi, 610 Winston Ct., St. Paul, Minn. 55118

[21] Appl. No.: 126,648

[22] Filed: Mar. 3, 1980

[51] Int. Cl.³ ............................................ A61B 10/00
[52] U.S. Cl. .................................................. 128/754
[58] Field of Search ................... 128/759, 753, 310; 433/102

[56] References Cited

U.S. PATENT DOCUMENTS

| | | | |
|---|---|---|---|
| 1,527,845 | 2/1925 | Daniel | 433/102 |
| 3,175,554 | 3/1965 | Stewart | 128/754 |
| 3,247,594 | 4/1966 | Nosonowitz | 433/102 |
| 3,598,108 | 8/1971 | Jamshidi et al. | 128/754 |
| 3,893,445 | 7/1975 | Hofsess | 128/754 |
| 4,044,468 | 8/1977 | Kahn | 433/102 |

FOREIGN PATENT DOCUMENTS

| | | | |
|---|---|---|---|
| 171975 | 11/1965 | U.S.S.R. | 128/754 |
| 249551 | 5/1970 | U.S.S.R. | 128/754 |

Primary Examiner—Kyle L. Howell
Assistant Examiner—N. A. Swisher
Attorney, Agent, or Firm—Orrin M. Haugen; Thomas J. Nikolai

[57] ABSTRACT

A biopsy sampling device, particularly adapted for bone marrow sampling, which includes a needle having a lumen formed therein, along with a removably disposed stylet. The needle is provided with a sharpened cutting edge, when desired, particularly when designed for bone marrow sampling. A gripping means is disposed about the proximal end of the needle, with the gripping means including a generally solid finger-gripping member with portions extending laterally of the needle, and with the finger-gripping member having a needle-receiving bore extending generally centrally through the member. The solid finger-gripping member has a pair of opposed channels formed along the outer surfaces thereof, with the axes of the channels being arranged at right angles, one to another, with one axis being generally parallel to the needle axis, and with the other axis being generally transverse to the needle axis. In an alternate embodiment, the biopsy sampling device is provided with a removable cap for maintaining the stylet in proper inserted disposition, with the distal end of the cap of the stylet being provided with means for achieving proper orientation of the stylet. Also, a guard is provided over the distal end of the body of the needle, with the guard having internal threads which mate with threads arranged along a distally extending projection sleeve of the finger-gripping member.

1 Claim, 12 Drawing Figures

BONE MARROW ASPIRATION NEEDLE

BACKGROUND OF THE INVENTION

The present invention relates generally to an improved biopsy sampling device, and more specifically to a biopsy sampling device which is particularly adapted for bone marrow biopsy procedures. The structure includes a needle portion having a lumen extending therethrough, along with a means for removably receiving a stylet within the needle lumen. A removable cap is provided at the proximal end of the device for maintaining the stylet in position within the needle lumen. A sharpened cutting edge is provided on the needle, when desired, for assisting in the bone marrow biopsy procedure. For achieving a firm finger grip, and for finger-gripping comfort, a finger-gripping member is provided adjacent the proximal end of the structure, with the opposed outer surfaces of the finger-gripping member having mutually perpendicular finger-gripping channels formed therein.

Generally, the finger-gripping channels are arranged in such a fashion that one channel has an axis generally parallel to the needle axis, with the opposed channel having an axis generally transversely thereto. This permits the surgeon to grip the member between the thumb and index finger, with the thumb being normally positioned within the groove parallel to the needle axis, and with the index finger being received in the groove generally perpendicular to the needle axis. Such an arrangement permits arcuate rotation of the structure so as to permit penetration of the bone, and entry into the zone wherein a bone marrow sample may be obtained pursuant to the biopsy procedure.

For achieving accuracy of penetration of the device, an internally threaded guard is provided which extends over a portion of the needle, with the threaded engagement of the guard on the body of the device being used to adjust the positioning of the guard to achieve accuracy of penetration.

The needle structure is preferably fabricated of stainless steel, as is the body of the stylet. The remaining components may be formed of a molded plastic, such as molded thermoplastic material such as methyl methacrylate, polystyrene, or the like, and other materials including metals may be employed.

SUMMARY OF THE INVENTION

Therefore, it is a primary object of the present invention to provide an improved finger-gripping member for biopsy needles, particularly for biopsy needles designed for bone marrow sampling procedures, and wherein the finger-gripping means provides finger receiving channels arranged with axes mutually perpendicular, one to the other.

It is a further object of the present invention to provide an improved bone marrow biopsy sampling device which includes a needle having a lumen formed therein, and with a stylet adapted for removable insertion therewithin, and wherein the distal end of the needle is provided with a sharpened bone cutting edge, and wherein the proximal end of the needle is provided with a finger-gripping member with finger-receiving grooves on the opposed outer surfaces thereof, and wherein the axes of the individual grooves extend at right angles, one to the other.

It is yet a further object of the present invention to provide an improved biopsy sampling device particularly adapted for bone marrow biopsy sampling procedures wherein a finger-gripping element is secured to the needle adjacent the proximal end thereof, and wherein the finger-gripping element contains generally arcuately contoured channels with axes disposed at mutually right angles, one to the other.

It is yet a further object of the present invention to provide an improved biopsy sampling device particularly adapted for bone marrow biopsy sampling procedures wherein a removable cap is provided for the proximal end of the device to assure constant positioning of a stylet within the lumen of the needle.

It is yet a further object of the present invention to provide an improved biopsy sampling device particularly adapted for bone marrow biopsy sampling procedures wherein a removable guard is provided along the needle, with the guard being arranged for adjustable positioning along the axis of the needle, for the purpose of achieving accuracy of penetration.

Other and further objects of the present invention will become apparent to those skilled in the art upon a study of the following specification, appended claims, and accompanying drawings.

DESCRIPTION OF ONE PREFERRED EMBODIMENT

Figure 1:
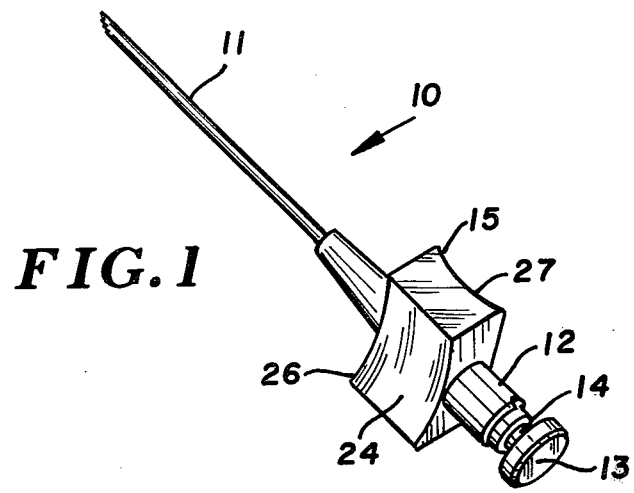
FIG. 1 is a perspective view of one preferred embodiment of the biopsy sampling device of the present invention, and illustrating the disposition of the finger-gripping member adjacent the proximal end thereof.
Figure 2:
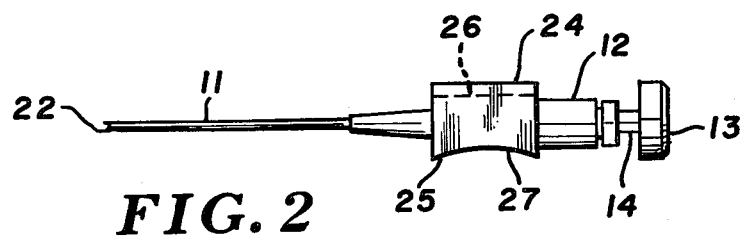
FIG. 2 is a side elevational view of the biopsy sampling device of FIG. 1, particularly when adapted for bone marrow procedures, and wherein the distal end of the needle is shown with scalloped cutting edges extending therearound.

In accordance with that preferred embodiment of the present invention illustrated in FIGS. 1–7, and with attention being directed to FIG. 1, the biopsy sampling device generally designated 10 includes a needle element 11 with a proximal hub portion 12 operatively coupled thereto. The needle device is shown with a stylet 28 retained therein, with the disc-shaped cap of the stylet being shown at 13, and the shank portion of the stylet being shown at 14. A finger-gripping member is shown at 15, and the details of this finger-gripping member will be more fully explained hereinbelow.

In order to couple the individual components forming the assembly together, the finger-gripping member 15 is in the form of a molded thermoplastic structure which envelops or encloses the proximal end of needle 11. A flare portion is provided as at 16 (see FIG. 6) in order to bind and assist in retention of the needle 11 within the member 15. The proximal end of the needle is further provided with a stylet-receiving hub as at 17, with the hub having detents formed therein as at 18 to receive a projection element 19 formed integrally on the shoulder element 20 of the stylet.

Needle 11 is provided with a lumen as at 21, with the lumen extending, of course, through the entire extent or length of needle 11 and finger-gripping element 15, and along through stylet-receiving hub 17. The distal end 22 of needle 11 is preferably serrated so as to assist in bone marrow biopsy procedures, thus assisting the surgeon in his efforts to penetrate the surface of the bone being sampled.

The present structure constitutes an improvement over those certain biopsy devices illustrated in my prior U.S. Pat. Nos. 3,598,108 and 3,628,524, and the present arrangement provides for added comfort and ease of manipulation due to the contours formed on finger-gripping element 15. Attention is now directed to FIGS. 2–6 of the drawings wherein the details of the finger-gripping member 15 are illustrated. Specifically, finger-gripping element 15 is provided with a pair of opposed outer surfaces as at 24 and 25, with each opposed outer surface having a groove formed therein, as at 26 and 27. Groove 27 has a base axis which extends generally perpendicularly to the axis of needle 11, while groove 26 has a base axis which extends generally parallel to the axis of needle 11. Each groove is formed so that the axis is generally midway between the respective outer edge surfaces of member 15.

Figure 4:
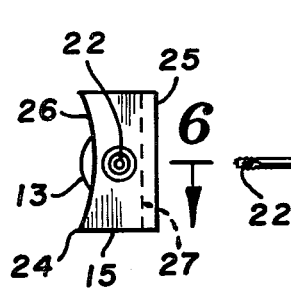
FIG. 4 is an end elevational view taken from the distal end of the device of FIG. 1.
Figure 3:
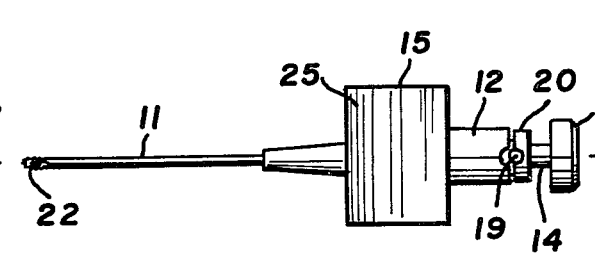
FIG. 3 is a view similar to FIG. 2, and illustrating the structure at a disposition rotated 90° from that view shown in FIG. 2.
Figure 5:
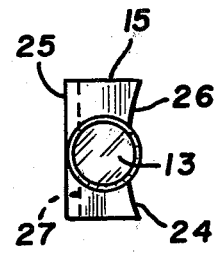
FIG. 5 is an end view taken from the proximal end of the device of FIG. 1, and illustrating the structure with the stylet positioned therewithin.
Figure 6:
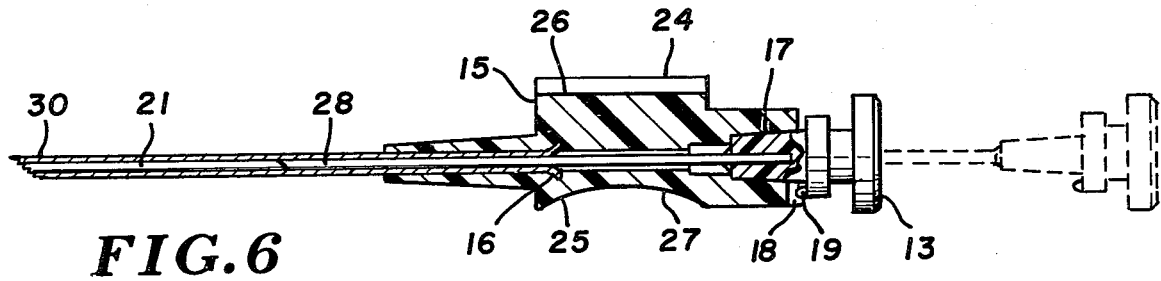
FIG. 6 is a sectional view taken through the axis of the device of FIG. 1, with portions being shown in plan view, specifically the stylet, with the view having been taken along the line and in the direction of the arrows 6—6 of FIG. 3, and further illustrating in phantom the stylet in partially retracted or removed disposition.
Figure 7:
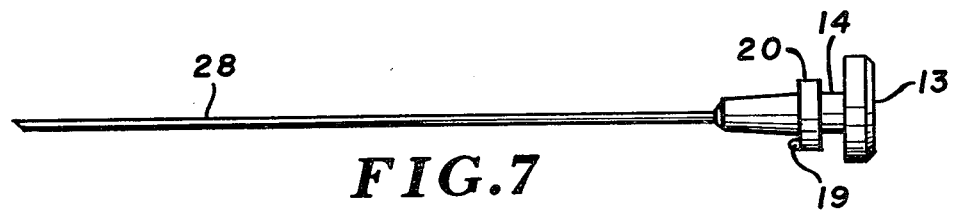
FIG. 7 is an elevational view of the stylet shown in FIGS. 1-6.

From a study of FIGS. 4 and 6, it will be seen that the grooves 26 and 27 are arcuately contoured, and have base axes which extend generally at right angles, one to the other.

In actual use, therefore, the surgeon will grasp the structure 10 with his thumb being received within channel or groove 27, and with his index finger being received in channel or groove 26. With this gripping arrangement, the surgeon may then arcuately rotate the entire assembly, so as to achieve penetration of the tissue or bone desired, with the arcuate rotation assisting in the overall manipulation and the overall completion of the procedure.

As has been indicated, the stylet is arranged to be removably received within needle 11, and when a procedure is commenced, the stylet is normally present. Once the site for obtaining the biopsy sample has been reached, the stylet is at least partially retracted, as is indicated in phantom in FIG. 6, and the needle assembly 10 then advanced to the desired extent in order to achieve and receive a sample within the distal end. For certain biopsy procedures, it is desired, of course, that the distal end of the needle, such as that portion indicated at 30 be flared outwardly so as to provide a chamber generally consistent with those shown in my earlier U.S. Pat. Nos. 3,598,108 an 3,628,524.

Figure 8:
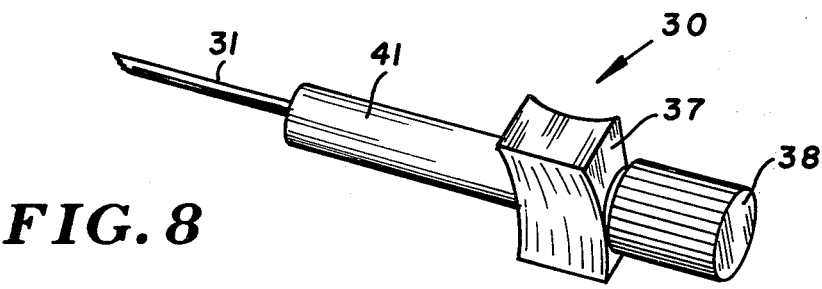
FIG. 8 is a perspective view of an alternate preferred embodiment of the biopsy sampling device of the present invention, and illustrating the structure with a stylet retaining cap in position thereon.

In accordance with that alternate preferred embodiment of the present invention as illustrated in FIGS. 8–12, and with attention being directed to FIG. 8, the biopsy sampling device generally designated 30 includes a needle element 31 with a proximal hub portion 32 operatively coupled thereto. The needle device is shown with a stylet 33 retained therein, with the disc-shaped cap of the stylet being shown at 34, with the rectangular shaped underside projection being shown at 35. The stylet also has a hyperbolic-shaped transition element for retaining the portion 33, as illustrated at 36. The finger-gripping portion 37 is shaped identically with that shown at 15 in the embodiment of FIGS. 1–7, and has been fully explained hereinabove.

The structure is provided with a removable cap as illustrated at 38, with the cap having an internally threaded portion as at 39 for securing cap 38 to the proximal end of the needle, specifically that portion illustrated proximally of the finger-gripping member 15. The purpose of the cap is to secure the stylet firmly in position during that portion of the procedure requiring the presence of the stylet.

The underside of the disc-shaped head of the stylet, as at 35, is preferably formed in a rectangular configuration in order to achieve proper orientation of the stylet within the lumen of the needle, inasmuch as the tip of the stylet is tapered in a fashion similar to that taper of the distal tip end of the needle. A corresponding or similar configuration to that of the underside surface 35 is formed in the proximal end of the device, as at 40. This configuration assists in maintaining the proper orientation of the stylet as indicated above.

Figure 9:
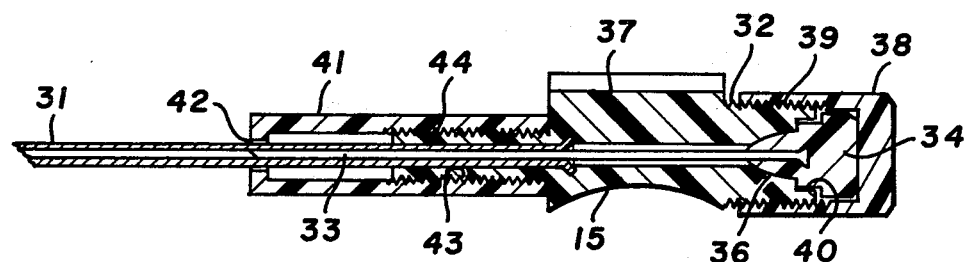
FIG. 9 is a longitudinal sectional view of the device illustrated in FIG. 8, and further showing an internally threaded guard member coupled to the body of the device and encompassing a portion of the length of the needle.
Figure 10:
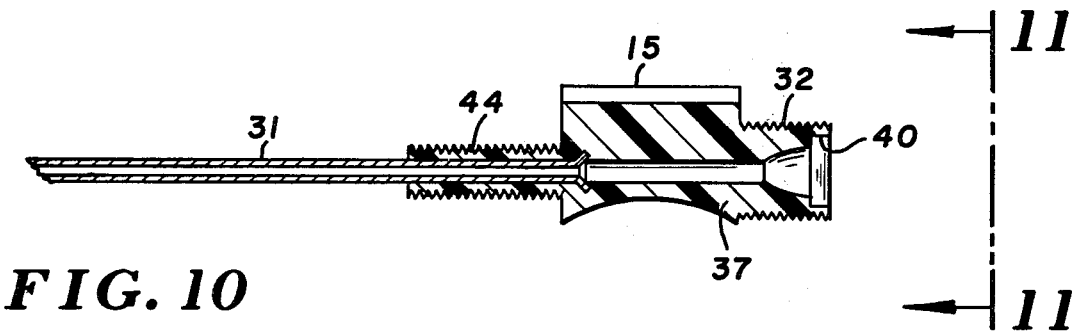
FIG. 10 is a vertical sectional view of the needle and gripping components only of the device illustrated in FIGS. 8 and 9, FIG. 10 showing the structure with the stylet, cap, and guard removed therefrom.
Figure 11:
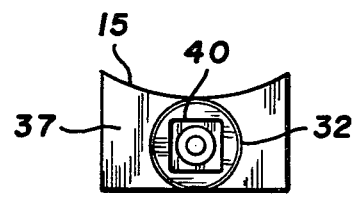
FIG. 11 is an end view of that portion of the device illustrated in FIG. 10.
Figure 12:
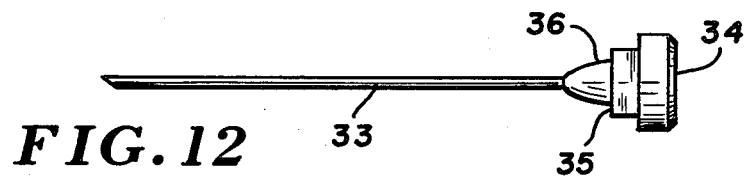
FIG. 12 is an elevational view of the stylet shown in FIG. 9.

Attention is now directed to FIG. 9 of the drawings wherein a threaded guard member is shown at 41. Guard 41 is in the form of a cylinder closed at one end, with the closed end having a small opening formed therein as at 42 to accommodate passage of the needle 31 therethrough. The internal portion of guard 41 is threaded as at 43, in order to mate with corresponding threads formed on the exterior portion of the sleeve projection 44, with the threads being illustrated in FIG. 9. This guard member is an improvement over that certain guard member shown in my prior U.S. Pat. No. 4,022,191, with the guard shown herein being infinitely adjustable.

I claim:

1. In combination with a bone marrow biopsy sampling device including a hollow needle, a stylet arranged to be removably disposed within the bore of said hollow needle and generally coextensive therewith, and with a sharpened cutting edge at the distal end of said hollow needle; gripping means disposed about the proximal end of said hollow needle and comprising:

(a) a generally solid finger-gripping member secured to said needle adjacent the proximal end thereof and being fast thereon, and with portions of said finger-gripping member extending laterally of said needle and having a needle-receiving bore formed generally along a first axis thereof and extending through said solid finger-gripping member, (b) said gripping means being of generally rectangular configuration having four faces aligned with the direction of said needle, the faces of a first opposite pair being generally plane and mutually parallel, and the faces of a second opposite pair intersecting the faces of said first pair and having grooves defined by concave cylinders, the base axes of one cylinder being parallel to the direction of said needle and the base axes of the other cylinder being orthogonal to said direction.

* * * * *